United States Patent [19]

Walkowiak et al.

[11] 4,308,190

[45] Dec. 29, 1981

[54] DENTAL MATERIALS BASED ON ORGANIC PLASTICS IN PASTE FORM

[75] Inventors: Michael Walkowiak, Leverkusen; Wolfgang Podszun, Cologne; Bernhard Leusner, Leverkusen; Carlhans Süling, Odenthal; Hans H. Schulz, Leichlingen, all of Fed. Rep. of Germany

[73] Assignee: Bayer Aktiengesellschaft, Leverkusen, Fed. Rep. of Germany

[21] Appl. No.: 95,722

[22] Filed: Nov. 19, 1979

[30] Foreign Application Priority Data

Nov. 24, 1978 [DE] Fed. Rep. of Germany ....... 2850917

[51] Int. Cl.³ .............................................. A61K 6/08

[52] U.S. Cl. .............................. 260/29.7 UA; 106/35; 260/29.6 RB; 260/29.7 UP; 260/42.52; 525/4; 525/226; 525/228; 525/297; 525/308; 525/309

[58] Field of Search .................. 525/226, 228, 4, 308, 525/309, 297; 106/35; 260/29.7 UA, 29.7 UP, 29.6 RB, 42.52

[56] References Cited

U.S. PATENT DOCUMENTS 3,539,533 11/1970 Lee et al. .............................. 106/35
3,911,581 10/1975 Dietz .................................... 106/35

*Primary Examiner*—Harold D. Anderson
*Attorney, Agent, or Firm*—Sprung, Felfe, Horn, Lynch & Kramer

[57] ABSTRACT

A dental material is provided based on organic plastics in paste form, which consists essentially of (a) a polymerizable binder, (b) a crosslinked bead polymer and (c) a fine-particled inorganic filler.

12 Claims, No Drawings

DENTAL MATERIALS BASED ON ORGANIC PLASTICS IN PASTE FORM

The present invention relates to novel dental materials based on filled organic plastics.

The use of filled plastics as materials for artificial teeth, bridges, crowns and dental fillings is known. For the preparation of dental fillings, these materials are usually employed as formulations of inorganic fillers, organic polymers, if appropriate and polymerisable binders.

The materials known hitherto have technological and clinical disadvantages because of their consistency and tackiness.

The material is introduced into the cavity by wiping in, and, after filling the cavity, in many cases some of the composition introduced is stripped from the wall of the cavity due to adhesion to the filling instrument. This phenomenom cannot as a rule be detected by the dentist and thus leads to non-parietal incomplete fillings, with the known disadvantages of them.

The increased tackiness of the filling materials known hitherto has a particularly adverse effect in the case of multi-surface cavities. Thus, as is known from the amalgam filling technique, perfect filling of the cavity is only possible if a filling material is introduced in portions. In this filling technique, small portions are first pressed parietally into the angles of the cavity, and only then is the cavity filled. A corresponding procedure using the plastic materials hitherto known is not possible.

Whilst in the case of single-surface fillings in the region of the front of teeth the shape of the surface is achieved by applying moulding strips, the shaping of occlusal surfaces with materials which have a tacky consistency presents difficulties. Thus the areas of the masticating surfaces could be shaped only coarsely in the case of the materials known hitherto. Shaping by rotating abrasive and polishing instruments was thus usually required after hardening. As is known, damage to the adjacent enamel areas is as a rule unavoidable during this process. The results of this are distortions in the relief of the masticating surface and in some cases occlusal disturbances.

Attempts have been made to produce the desired shape of the surface by producing a "carvable" consistency. However, this "carvable" property only results when a certain degree of polymerisation has already been achieved. If the filling material is worked in this state, the filling surface can crack open or tear and thus damage to the filling cannot be excluded. These cracks, produced by "carving" can be openings for microorganisms and for dyestuffs, with the known effects. Moreover, working of materials which are already partly polymerised can lead to interference with the polymerisation.

According to the present invention there is provided a dental material based on organic plastics in paste form, which consists essentially of (a) a polymerisable binder, (b) a crosslinked bead polymer and (c) a fine-particled inorganic filler.

It has been found, surprisingly, that these pastes are outstandingly suitable as a dental filling material.

The materials according to the invention can be prepared in a consistency which makes processing as is customary in the amalgam filling technique possible, that is to say that can be (a) pressed in and (b) shaped.

The following remarks relate to the aspect (a) of filling technique:

With the materials according to the invention, it is possible, using a non-tacky, firm consistency which is suitable for pressing in, to fill single-surface and multisurface cavities parietally in several portions. The special property of the material means that there is no formation of layers when filling is effected in portions, that is to say the individual portions bond to one another homogeneously.

After introduction of a particular portion into the cavity and the pressing-in or adapting thereof, this portion remains in position without changing its shape, that is to say it cannot even be deformed elastically.

Furthermore, because of the special consistency, the cavity can be filled using so-called amalgam guns without the filling material being pulled off again from the wall of the cavity or continuing to adhere to the nozzle of the gun.

The following remarks relate to the aspect (b) of filling technique:

The materials according to the invention exhibit a consistency which allows shaping by instruments and is already obtained immediately after the mixing process. This consistency makes it possible for the occlusal individual form of the chewing surface to be shaped, after filling the cavity, by means of suitable instruments, for example of plastic or of metal, such as are used in the amalgam filling technique.

The paste-like dental materials, according to the invention, based on organic plastics, are transformed, by hardening, into solid substances which then have the particular advantage that they can readily be polished.

For the preparation of the dental materials in accordance with the invention, from 20 to 60, and preferably from 25 to 50, parts by weight polymerizable binder, from 20 to 75, and preferably from 30 to 65, parts by weight crosslinked bead polymers, from 5 to 50, and preferably from 5 to 28, parts by weight inorganic filler, and from 0.01 to 5 parts by weight initiators are mixed to form a paste.

To facilitate paste preparation, inhibitors or light stabilizers may be added. For specific indications, it may be advisable to add also dyes.

Preferred polymerisable binders for the dental materials according to the invention are the esters of methacrylic acid and monohydric and polyhydric alcohols, optionally mixed with other vinyl monomers. It is particularly favourable if the content of methacrylic acid esters is over 80%, especially if 50% by weight of esters of methacrylic acid have two or more polymerisable double bonds.

Examples of suitable esters of methacrylic acid which may be mentioned are aliphatic and cycloaliphatic esters, such as methyl methacrylate, ethyl methacrylate and cyclohexyl methacrylate.

Very particularly suitable binders are furthermore esters of polyhydric alcohols with a molecular weight of 190–10,000, preferably esters of bivalent and trivalent alcohols with a molecular weight of 190–800, such as, for example, ethylene glycol dimethylacrylate, triethylene glycol dimethacrylate, neopentylglycol dimethacrylate or trimethylolpropane trimethacrylate, and moreover urethane and ureidopolymethacrylates, which are accessible by reacting hydroxyalkyl methacrylates or aminoalkyl methacrylates with polyisocyanates, for example the compound.

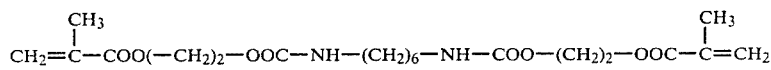

Very good pastes are obtained if at least a proportion of the binder used consists of compounds of the bis-GMA type, of the formula

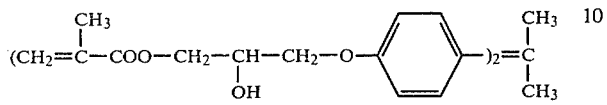

Dental filling compositions with a good consistency and a high level of mechanical strength are obtained, in particular, if mixtures of various methacrylic acid esters are used as the binder, for example mixtures of 20–70 parts by weight of Bis-GMA and 80–30 parts by weight of triethyleneglycoldimethacrylate.

Inhibitors or light stabilisers can be added to the monomers to facilitate compounding the pase. For certain indications it can be appropriate to add dyestuffs to the binder system.

The crosslinked bead polymers employed for the preparation of the paste should consist of polymerised methacrylic acid esters, preferably methacrylic acid methyl ester, to the extent of more than 50% by weight. Suitable monomers having a crosslinking action are polyvinyl compounds which can be copolymerised with methyl methacrylate, such as, for example, ethylene glycol dimethacrylate or divinylbenzene, and the proportion of crosslinking agent should be 2 to 35% by weight of the monomer mixture. Besides the crosslinking agent, other monomers can be copolymerised in the bead polymer for example in order to influence the swelling properties of the bead polymer or to modify the mechanical properties of the hardened dental plastic. The average particle size of the bead polymers employed should preferably be between 10 and 100$\mu$: the range from 15 to 70$\mu$ is particularly favourable.

Bead polymers as described in European patent applications (Specification Ser. No. (Le A 19 287)) and (Specification Ser. No. 79 10 42 46.8 (Le A 19 290)), are furthermore particularly suitable for the paste formulation. The use of bead polymers filled with inorganic fillers as described in European patent application 79 10 42 53.4. (Specification Ser. No. (Le A 19 290)) is particularly advantageous since dental materials can be obtained in which both the bead polymer and the interstices between the beads equally contain inorganic filler, whereby a high degree of homogeneity in the hardened material is achieved.

Such polymers are bead polymers having a mean bead dimeter of from 10 to 200$\mu$ of one or more polymerized viscous methacrylates and/or dimethacrylates having a viscosity of from 0.5 to 500 Pa.s and, optionally, up to 20% by weight of one or more other vinyl monomers are furthermore particular suitable for the paste formulation.

Polymer beads having an average bead diameter of from 5 to 500$\mu$, consisting of an inorganic fine-particled filler and polymerized (meth)acrylic acid esters, having a viscosity of from 0.1 to 10 Pa.s, are also particularly suitable for the paste formulation.

Suitable fine-particled inorganic fillers for the dental materials according to the invention are, above all, silicon dioxide, aluminium oxide, silicates and silicate glasses, as long as their average particle size is in the range of 1 m$\mu$-1$\mu$. Preferred fine-particled inorganic filler consists of silicic acid. It is particularly favourable to use amorphous silicon dioxide which is obtained by flame pyrolysis, and in particular amorphous silicon dioxide with a primary particle size of 5–30 m$\mu$ and a specific surface area, measured by the BET method, of 40–400 m$^2$/g.

The fine-particled inorganic filler can be after-treated ("silanised") with special silane adhesive promoters, for example with vinyltrimethoxy-silane or with trimethoxy-(3-methacryloyloxypropyl)-silane, in order to improve the bond between the inorganic filler and the organic matrix, but this after-treatment step is not absolutely necessary for the preparation of the dental materials according to the invention.

Preferred dental materials are those in which the proportion of crosslinked bead polymer and fine-particled inorganic filler together is 52 to 80% by weight. Also preferred are dental materials in which the proportion of fine-particled filler is 5 to 50%, especially 5 to 28%, by weight.

The customary starter systems can be used for hardening the dental materials according to the invention, that is to say systems which supply free radicals, anions or cations and which can trigger off free radical, anionic or cationic polymerisation. Peroxides or aliphatic azo compounds are particularly suitable in the case of systems which supply free radicals, for example, benzoyl peroxide, lauroyl peroxide or azoisobutyric acid dinitrile, which normally are used in amounts ranging from 0.1 to 5 wt. %. While the cure at elevated temperature is carried out with the aid of peroxides or other radical initiators alone, curing at room temperature requires the addition of accelerators, preferably aromatic amines. Suitable accelerators are N-N-substituted toluidines and xylidines, such as NN-dimethyl-p-toluidine or NN-bis (2-hydroxyethyl)xylidine. A good cure is obtained with an 0.5 to 3% amine addition. An advantageous form for a peroxide/accelerator-activated system is the two-paste form, one of the pastes incorporating the radical initiator and the other the accelerator, and curing being initiated by mixing of the two pastes.

Curing by means of UV light or visible light, with appropriate sensitization, is also a very good method. Suitable photoinitiators are, for example, benzophenone and its derivatives, benzoin and its derivatives such as benzoin ether, anthraquinone, and aromatic disulfides.

EXAMPLE 1

Preparation of a bead polymer from methyl methacrylate, ethlene glycol dimethacrylate and ethyl acrylate. Polymerisation Reaction vessel: 6 liter autoclave with a double-anchor stirrer.
Solution I: 2,500 ml of distilled water
(Dispersing agent solution): 500 ml of a 7.5% strength aqueous solution of the copolymer of 1 part by weight of methacrylic acid and 1 part by weight of methyl methacrylate, with a pH of 6 and viscosity of 3,650 cp.

Solution II: 765 g of methyl methacrylate, 90 g of ethyl acrylate, 45 g of ethylene glycol dimethacrylate, 4.5 g of benzoyl peroxide and 4.5 g of lauroyl peroxide.

Solution I is initially introduced into the autoclave and is stirred for 5 minutes. Solution II is added all at once, with the stirrer stopped, and the autoclave is flushed with nitrogen. The pressure is then increased to 5 bars of nitrogen, the stirrer speed is adjusted to 400 rpm and the mixture is heated to 80° C. When the exothermic reaction starts, the mixture is cooled to an extent such that the temperature remains below 90° C. The mixture is subsequently stirred at 80° C. for 2 hours.

Working up

The mixture is let down and diluted to 10 l with distilled water. After adding 180 g of glacial acetic acid, it is heated to 90°–100° C. for 15 minutes. The bead polymer which precipitates is filtered off after cooling, washed by stirring three times in 5 l of distilled water at a time, and dried at 60° C.

Yield: 845 g
Average bead diameter: 25μ.

EXAMPLE 2

Preparation of a bead polymer filled with amorphous silicon dioxide

The same reaction vessel and the same dispersing agent solution as in Example 1 are used.

Solution II: 684 g of methyl methacrylate, 36 g of ethylene glycol dimethacrylate, 308 g of silanised amorphous silicon dioxide (surface area, measured by the BET method, 170 m$^2$/g) and 7.2 g of benzoyl peroxide.

The polymerisation and working up are carried out as in Example 1. 866 g of a bead polymer with an average particle size of 45μ are obtained.

EXAMPLE 3

Paste-like dental materials according to the invention (A) Peroxide paste 250 g of the bead polymer from Example 1, 104 g of silanised amorphous silicon dioxide (surface area, measured by the BET method, 170 m$^2$/g), 96 g of bis-GMA ("Nupol" 46–4005 from Messrs. Freeman Chemical), 52 g of triethylene glycol dimethacrylate and 2.7 g of benzoyl peroxide.

The individual components are put into a kneader and kneaded intensively for 60 minutes, a vacuum of about 20 mm Hg being applied during the last 10 minutes. A kneadable mass with a particularly firm consistency is obtained in this manner.

(B) Amine paste

The bead polymer, bis-GMA and triethylene glycol dimethacrylate are employed in the same amounts as in the case of peroxide paste (A), and are processed. However instead of the peroxide, 1.8 g of N,N-bis-(2-hydroxypropyl)-3,5-dimethylaniline are employed.

(C) Paste-like composition for filling teeth

Equal parts (for example 200 mg each) of the amine paste and peroxide paste are mixed intensively for 30 seconds. The resulting mixture is outstandingly suitable as a dental filling material. It hardens in a few minutes with little shrinkage on polymerisation.

EXAMPLE 4

Paste-like dental materials according to the invention

An amine paste and a peroxide paste are prepared from, in each case, 110 g of the bead polymer according to Example 2, 28 g of silanised amorphous silicon dioxide (surface area, measured by the BET method, 170 m$^2$/g), 47 g of bis-GMA and 25 g of triethylene glycol dimethacrylate, using 1.5 g of bis-o-toluyl peroxide or 1.2 g of N,N-bis-(2-hydroxypropyl)-3,5-dimethylaniline, by a procedure corresponding to that in Example 3.

This material is mixed like the material from Example 3. A mixture which is outstandingly suitable as a dental filling material is likewise obtained.

EXAMPLE 5

Pasty dental material in accordance with the invention

A dental material is prepared by the procedure set forth in Example 3 from 230 g bead polymer according to Example 1,
100 g silanized amorphous silicon dioxide (surface area, measured by the BET method, 170 m$^2$/g),
96 g bis-GMA,
52 g triethylene glycol dimethacrylate, and
0.75 g benzoyl peroxide.

This material, suited for the fabrication of dentures, may be cured at elevated temperature while being shaped. Suitable curing conditions are 130° C./10 min.

EXAMPLE 6

Pasty dental material in accordance with the invention

A pasty mixture is prepared by the procedure set forth in Example 3 from 200 g bead polymer according to Example 1,
50 g silanized amorphous silicon dioxide (surface area, measured by the BET method, 170 m$^2$/g),
80 g triethylene glycol dimethacrylate,
120 g bis-GMA, and
4 g benzoin isopropylether.

This material is extremely well suited for use as a dental filling material. It will cure when exposed to UV light (Uviolite lamp of the Espe company) within 40 sec in layers 2.5 mm thick.

What is claimed is:

1. A dental material in paste form which consists essentially of
    (a) at least one polymerizable binder wherein at least 50% by weight of said binder is at least one ester of methacrylic acid and a monohydric or polyhydric alcohol,
    (b) at least one cross-linked bead polymer plastic made from at least one ester of methacrylic acid and a monohydric or polyhydric alcohol and
    (c) a fine-particled inorganic filler.

2. The dental material according to claim 1 wherein more than 80% by weight of the polymerizable binder is methacrylic acid ester or esters.

3. The dental material according to claim 2 wherein at least 50% by weight of the polymerizable binder is at least one ester of methacrylic acid with two or more polymerizable ethylenically unsaturated double bonds.

4. The dental material according to claim 1 or 2 wherein the polymerizable binder is a mixture of said esters.

5. The dental material according to claim 1 or 2 wherein said cross-linked bead polymer has been prepared by polymerizing one or more vinyl monomers, at least 50% by weight of said monomers being at least one ester of methacrylic acid.

6. The dental material according to claim 1 or 2 in which the crosslinked bead polymer has an average particle size of 10 to 100μ.

7. The dental material according to claim 1 or 2 in which the fine-particled inorganic filler has an average particle size <1μ.

8. The dental material according to claim 7 in which the fine-particled inorganic filler consists of silicon dioxide.

9. The dental material according to claim 7, in which the fine-particled inorganic filler is silanized.

10. The dental material according to claim 1 or 2 in which the proportion of crosslinked bead polymer and fine-particled inorganic filler together is 52 to 80% by weight of said dental material.

11. The dental material according to claim 1 or 2 in which the proportion of fine-particled inorganic filler is 5 to 50% by weight of said dental material.

12. The dental material according to claim 10, in which the proportion of fine-particled inorganic filler is 5 to 28% by weight of said dental material.

* * * * *